United States Patent [19]

Hwang

[11] Patent Number: 5,541,093
[45] Date of Patent: Jul. 30, 1996

[54] VAPOR STATE ESTERIFICATION USING ENZYMES

[75] Inventor: Soon O. Hwang, Seoul, Rep. of Korea

[73] Assignee: Yukong Ltd., Seoul, Rep. of Korea

[21] Appl. No.: 393,183

[22] Filed: Feb. 23, 1995

[30] Foreign Application Priority Data

Feb. 26, 1994 [KR] Rep. of Korea .................. 94-3549

[51] Int. Cl.$^6$ ........................................................ C12P 7/62
[52] U.S. Cl. ........................................... 435/135; 435/198
[58] Field of Search ..................................... 435/135, 198

[56] References Cited

U.S. PATENT DOCUMENTS 5,209,940  5/1993  Champagne et al. ................... 568/916

OTHER PUBLICATIONS

APS Japanese ABS 63-133991 (Jun. 6, 1988) Kobori et al APS Pub Date Oct. 14, 1988 Kao Corp.
Biotech ABS. 94-12416 Martin et al "Enzyme Microb. Tech" (1994) 16,9, 785-90.
Biotech ABS 94-06962 Hwang et al "Biotech. Lett." (1994) 16,4, 379-84.
Biotech ABS 92-05370 Parvaresh et al "Biotech Bioeng" (1992) 39,4, 467-73.

*Primary Examiner*—Herbert J. Lilling
*Attorney, Agent, or Firm*—Abelman, Frayne & Schwab

[57] ABSTRACT

There is disclosed a method for the preparation of ester compound. It is distinguished by comprising reaction of an alcohol with an organic acid in the vapor state and at a temperature of 25° to 55° C., in the presence of lipase. Unlike production in aqueous solutions, the ester compounds prepared according to the method have no difficulty in separating from the reaction system because they are in the vapor state. Accordingly, the method is suitable for mass production.

3 Claims, No Drawings

VAPOR STATE ESTERIFICATION USING ENZYMES

BACKGROUND OF THE INVENTION

1. Field of the Invention

The present invention relates, in general, to a method for the preparation of ester compound and, more particularly, use of enzyme to prepare ester compounds from vapor state substrates.

2. Description of the Prior Art

Ester compounds as used herein include ethyl acetate, n-propyl acetate, isopropyl acetate, n-butyl acetate, isobutyl acetate, ethyl propionate, ethyl butyrate, which all are used as natural flavor.

Lipase, an esterase, catalyzes the production of ethyl acetate (Langrand et al., Biotechnol, Lett., 12, 581, 1990), as illustrated by the following reaction formula:

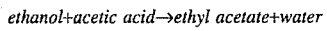

To speak generally, this reaction is expressed as follows:

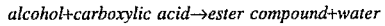

It is possible to synthesize ester compounds in chemically synthetic processes. However, as natural compounds are increasingly demanded, there have been undertaken extensive researches and studies for utilizing ferments of microorganism or enzymes, to produce ester compounds in a large quantity (Armstrong et al., Biotechnol. Bioeng. 26, 1038, 1984; Williams et al., Ann. New York Acad. Sci., 542, 406, 1988; Murray and Duff, Appl. Microbiol. Biotechnol. 33, 202, 1990; Fukuda et al., Curr. Genet., 20, 49, 1991; Fukuda et al., J. Ferm. Bioeng. 75, 288, 1993). The reactions suggested in supra articles are carried out in aqueous solution. It is reported that the reactivities of the enzymes are confirmed. However, those processes are problematic in that the solubility of ester compound produced in water is extremely low.

Enzymatic reaction systems (Langrand et al., Biotechnol. Lett. 12, 581, 1990; Welsh and Williams, Enzyme Microbiol. Technol., 12, 743, 1990; Carta et al., Biotechnol. Bioeng., 37, 1004, 1991; Manjon et al., Biotechnol. Lett., 13, 339, 1991) show mass transfer limitation in solvents other than water and it is difficult to isolate the products from the solvents (Dordick, Enzyme Microbiol. Technol., 11, 194, 1989; Kery et al., J. Chem. Tech. Biotechnol., 48, 201, 1990).

As explained above, it is recognized that solubility of ester compounds in aqueous solutions is low and recovery of them from other solvents (reaction media) is not easy. Taking advantage of vaporization of the substrates (reactants) and the ester compounds (products), the present inventor made an attempt to catalyze the reaction in the vapor state.

There had been an attempt to react ethanol vapor with acetic acid vapor in the presence of lipase. However, it is reported that, when ethanol vapor is treated with acetic acid vapor at 30° C. in the presence of lipase from *Candida rugosa*, ethyl acetate is not produced (Ross and Schneider, Enzyme Microbiol. Technol.. 13, 370, 1991). It is believed that this is attributed to a fact that water content in the lipase is high.

SUMMARY OF THE INVENTION

Therefore, an object of the present invention is to overcome the above problems encountered in prior arts and to provide a method for the preparation of natural ester compound from alcohols and organic acids in the vapor state, capable of taking advantage of lipase.

It is another object of the present invention to provide a method for the preparation of natural ester compound, applicable to industrialization.

In accordance with the present invention, the above objects could be accomplished by a provision of a method for the preparation of ester compounds, comprising reaction of an alcohol with an organic acid in the vapor state in the presence of lipase.

These and other objects and advantages of the present invention will be more apparent as following description proceeds.

DETAILED DESCRIPTION OF THE INVENTION

Lipases used in the present invention include those derived from pancreas of pig, enzymes obtained from microorganisms at powder or liquid phase, immobilized lipases, and cells or immobilized cells containing lipase and preferably have a water content ranging from about 1 to about 25% by weight.

A more detail is shown as given in the following Table I.

TABLE I

| Kind of Lipase | Concentration of Ethyl acetate (μM) |
|---|---|
| Lipase GL (sold by Amano Co., Ltd.) | 0.331 |
| Lipase AY (sold by Amano Co., Ltd.) | 22.543 |
| Lipase CES (sold by Amano Co., Ltd.) | 31.703 |
| Lipase CE (sold by Amano Co., Ltd.) | 1.675 |
| Lipase PS (sold by Amano Co., Ltd.) | 5.182 |
| Lipase 7023C (sold by Röhm Co., Ltd.) | 3.997 |
| Lipase 22-12E (sold by Röhm Co., Ltd.) | 3.416 |
| Lipase (sold by Novo Co., Ltd.) | 28.716 |
| Lypozyme IM (sold by Novo Co., Ltd.) | 0.666 |
| Lipase MY | 40.010 |
| Lipase D* (sold by Amano Co., Ltd.) | 0.219 |
| Lipase EAP 15 | 0.304 |
| Lipase R (sold by Amano Co., Ltd.) | 1.772 |
| Lipase Jozo (sold by Toyo Co., Ltd.) | 17.457 |

The expression "ester compounds" as used in the present specification mean ethyl acetate, n-propyl acetate, isopropyl acetate, n-butyl acetate, isobutyl acetate, ethyl propionate, and ethyl butyrate.

In case of applying the method according to the present invention to a batch format, the reaction can be performed by, for example, charging lipase in a 15 ml vial with a silicon rubber septum and injecting ethanol vapor and acetic acid vapor into the vial by means of a gas-tight syringe (commercially available from Hamilton Co. Ltd.) at room temperature or more. At the moment, the temperature of outside of the vial may be ordinary temperature and preferably maintained in a range of 25° to 55° C. 4 to 10 hours is enough for the reaction.

It was observed that water, a product of the reaction, acts as a suppressor for the reaction. Accordingly, the present inventor found that the reaction can proceed in a fed-batch or continuous manner with the proviso that the concentration of water is so maintained as not to suppress the reaction.

Rapid cooling of the reactor into 5° C. or less liquidizes ethyl acetate with the aim of recovering the product.

Produced ester compounds were quantitatively measured by means of gas chromatography such as that sold by Hewlett-Packard Co. Ltd., under the trademark designation "Model 5890". In this connection, a capillary column (inner diameter 0.53 mm, film thickness 1.0 mm, length 30 m) packed with Carbowax (trademark)-coated silica was heated at 60° C. for 5 min. and up to 160° C. in a rate of 20° C. per min, and the temperature raise was stopped at this temperature for 5 min. Nitrogen gas with a flowing rate of 5 ml per min. was employed as a carrier. FID was maintained at 200° C. Ethanol, acetic acid and ethyl acetate were detected at 3.9, 11.5 and 3.4 min., respectively. Under the above experimental conditions, ester compounds were produced and thus, the present invention was realized.

The preferred embodiment of the present invention will now be further described with reference to the following specific example.

EXAMPLE 1

Into 15 ml vial with a silicon rubber septum, 10 mg of lipase derived from pancreas of pig, commercially available from Sigma Co., Ltd. was charged. Subsequently, 5 ml of ethanol (commercially available from Merck Co. Ltd.)-saturated vapor and 5 ml of acetic acid (commercially available from Merck Co., Ltd.)-saturated vapor were injected by means of respective syringes for gas into the vial. Thereafter, 100 µl of the resulting gas was taken from the vial at predetermined intervals and subjected to gas chromatography with the aim of quantitative analysis.

The analysis results are given as shown in the following Table II.

TABLE II

| Amount of Produced Ethyl acetate by Times | |
|---|---|
| Time | Ethyl acetate (µM) |
| 1.5 | 2.4 |
| 3 | 4.1 |
| 4.5 | 4.8 |
| 6 | 5.2 |
| 8 | 5.4 |
| 9.5 | 5.1 |
| 11 | 5.1 |

As apparent from the above Table II, maximum production amount appears after 8 hours.

EXAMPLES 2 THROUGH 7

10 mg of lipases derived from pancreas of pig were treated in such a manner that their water contents might be 0.96, 2.96, 9.96, 18.11, 24.96 and 30%. Thereafter, the same reaction as in Example 1 was repeated. The water content was controlled according to a method suggested in Biotechnol. Bioeng., 37, 1004, 1989, to Barzana et al., in which the vial containing dry lipase was exposed to air in a vessel containing saturated saline.

Under the same conditions as in Example 1, alcohol vapor and acetic acid vapor were reacted with each other for 8 hours, followed by analysis. Ethyl acetate was produced in a concentration of 1.4, 5.4, 4.7, 3.5, 2.8 and 0.01 µM. When the water content was 2.96%, ethyl acetate was produced in the largest amount. In addition, it was found that over 25% of water content restrained the reaction.

EXAMPLES 8 THROUGH 11

Ethyl acetate was produced in the same manner as in Example 1, except that the reaction temperature was changed into 25°, 35°, 45° and 55° C. Initial reaction rates at the temperatures were 0.10, 0.14, 0.15 and 0.17 µM/hr/enzyme mg. From these Examples, it was apparent that the reaction could proceed at 55° C.

EXAMPLES 12 THROUGH 25

Into 15 ml vial with a silicon rubber septum, 10 mg of lipases with a water content of 4%, derived from microorganisms, as given in Table III, was charged. Subsequently, 5 ml of ethanol (commercially available from Merck Co., Ltd.)-saturated vapor and 5 ml of acetic acid (commercially available from Merck Co., Ltd.)-saturated vapor were injected by means of respective syringes for gas into the vial and reacted with each other for 5 hours. Results were obtained from a quantitative analysis and are given in the following Table III.

TABLE III

| Example No. | Kind of Lipase | Concentration of Ethyl acetate (µM) |
|---|---|---|
| 12 | Lipase GL(sold by Amano Co., Ltd.) | 0.331 |
| 13 | Lipase AY(sold by Amano Co., Ltd.) | 22.543 |
| 14 | Lipase CES(sold by Amano Co., Ltd.) | 31.703 |
| 15 | Lipase CE(sold by Amano Co., Ltd.) | 1.675 |
| 16 | Lipase PS(sold by Amano Co., Ltd.) | 5.182 |
| 17 | Lipase 7023C(sold by Röhm Co., Ltd.) | 3.997 |
| 18 | Lipase 22-12E(sold by Röhm Co., Ltd.) | 3.416 |
| 19 | Lipase(sold by Novo Co., Ltd.) | 28.716 |
| 20 | Lypozyme IM(sold by Novo Co., Ltd.) | 0.666 |
| 21 | Lipase MY | 40.010 |
| 22 | Lipase D*(sold by Amano Co., Ltd.) | 0.219 |
| 23 | Lipase EAP 15 | 0.304 |
| 24 | Lipase R(sold by Amano Co., Ltd.) | 1.772 |
| 25 | Lipase Jozo(sold by Toyo Co., Ltd.) | 17.457 |

EXAMPLE 26

Example 1 was repeated using propionic acid instead of acetic acid. The produced ethyl propionate was detected at 4.6 min.

EXAMPLE 27

Example 1 was repeated using butyric acid instead of acetic acid. The produced ethyl butyrate was detected at 5.6 min.

EXAMPLE 28

Example 1 was repeated using propanol instead of ethanol. The produced propyl acetate was detected at 5.2 min.

EXAMPLE 29

Example 1 was repeated using isopropanol instead of ethanol. The produced isopropyl acetate was detected at 3.6 min.

EXAMPLE 30

Example 1 was repeated using n-butanol instead of ethanol. The produced n-butyl acetate was detected at 5.9 min.

EXAMPLE 31

Example 1 was repeated using isobutanol instead of ethanol. The produced isobutyl acetate was detected at 5.4 min.

As described hereinbefore, the method according to the present invention is able to prepare ester compounds from vaporized alcohols and organic acids by use of lipase derived from pancreas of pig.

Other features, advantages and embodiments of the present invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A method for the preparation of ester compounds, comprising reaction of an alcohol in the vapor state with an organic acid in the vapor state in the presence of lipase which has a water content of about 1 to about 25% by weight, at a temperature ranging from about 25° to about 550° C.

2. The method in accordance with claim 1, wherein said alcohol in the vapor state is selected from the group consisting of ethanol, n-propanol, isopropanol, n-butanol and isobutanol.

3. The method in accordance with claim 1, wherein said organic acid in the vapor state is selected from the group consisting of acetic acid, propionic acid and butyric acid.

* * * * *